United States Patent [19]
Sarver et al.

[11] Patent Number: 6,120,150
[45] Date of Patent: Sep. 19, 2000

[54] DEVICE AND METHOD FOR MAPPING THE TOPOGRAPHY OF AN EYE USING ELEVATION MEASUREMENTS IN COMBINATION WITH SLOPE MEASUREMENTS

[75] Inventors: Edwin J. Sarver, Merritt Island, Fla.; Charles R. Broadus, Ogden, Utah

[73] Assignee: Orbtek, Inc., Salt Lake City, Utah

[21] Appl. No.: 09/370,559

[22] Filed: Aug. 9, 1999

Related U.S. Application Data

[63] Continuation of application No. 08/841,534, Apr. 24, 1997.

[51] Int. Cl.$^7$ ........................................... A61B 3/00
[52] U.S. Cl. ............................... 351/247; 351/212
[58] Field of Search .................. 351/205, 212, 351/211, 246, 247

[56] References Cited

U.S. PATENT DOCUMENTS

| Re. 27,475 | 9/1972 | Volk | 351/212 |
|---|---|---|---|
| D. 345,213 | 3/1994 | Shalon et al. | 351/221 |
| 1,006,825 | 10/1911 | Buchhop | 351/212 |
| 1,750,931 | 3/1930 | Kellner et al. | 351/212 |
| 2,174,308 | 9/1939 | Hartinger | 351/212 |
| 2,250,521 | 7/1941 | Boeder | 351/205 |
| 3,248,162 | 4/1966 | Knoll | 351/205 |
| 3,290,927 | 12/1966 | Gambs | 351/205 |
| 3,486,812 | 12/1969 | Volk | 351/211 |
| 3,536,384 | 10/1970 | Cocks | 351/211 |
| 3,598,478 | 8/1971 | Townsley | 351/212 |
| 3,609,017 | 9/1971 | Nuchman | 351/211 |
| 3,634,003 | 1/1972 | Guyton | 351/221 |
| 3,797,921 | 3/1974 | Kilmer et al. | 351/212 |
| 3,895,860 | 7/1975 | Townsley | 351/212 |
| 3,932,030 | 1/1976 | Hasegawa et al. | 351/212 |
| 4,019,813 | 4/1977 | Cornsweet et al. | 351/205 |
| 4,157,859 | 6/1979 | Terry | 351/212 |
| 4,159,867 | 7/1979 | Achatz et al. | 351/212 |
| 4,172,639 | 10/1979 | Lang et al. | 351/212 |
| 4,256,385 | 3/1981 | Cohen et al. | 351/212 |
| 4,410,242 | 10/1983 | Muller et al. | 351/212 |
| 4,426,141 | 1/1984 | Holcomb | 351/212 |
| 4,456,348 | 6/1984 | Schulz et al. | 351/212 |
| 4,490,022 | 12/1984 | Reynolds | 351/212 |
| 4,491,398 | 1/1985 | Karickhoff | 351/212 |
| 4,540,254 | 9/1985 | Humphrey | 351/205 |
| 4,569,576 | 2/1986 | Karpov et al. | 351/205 |
| 4,597,648 | 7/1986 | Feldon et al. | 351/205 |
| 4,669,466 | 6/1987 | L'Esperance | 351/205 |
| 4,685,140 | 8/1987 | Mount, II | 351/211 |
| 4,772,115 | 9/1988 | Gersten et al. | 351/211 |
| 4,779,973 | 10/1988 | Miller et al. | 351/211 |
| 4,799,784 | 1/1989 | Safir | 351/212 |
| 4,817,432 | 4/1989 | Wallace et al. | 351/212 |
| 4,834,529 | 5/1989 | Barrett | 351/212 |
| 4,863,260 | 9/1989 | Gersten et al. | 351/212 |

(List continued on next page.)

OTHER PUBLICATIONS

Koch et al., "Introduction To Corneal Topography", *Corneal Topography The State of the Art*, pp. 3–15, 1995.

Orbtek brochures, "Orbscan Total Anterior Chamber Eye Exam", 7 pages.

*Primary Examiner*—Huy Mai
*Attorney, Agent, or Firm*—Trask Britt

[57] ABSTRACT

In an inventive method for mapping the topography of an eye, elevation measurements of the eye are collected using a slit beam diffuse reflection system, such as an ORBSCAN™ device. An approximating b-spline surface is then fitted to the elevation measurements. Slope measurements of the eye are collected using a Placido-based reflective system, but the slope measurements are referenced to points on the b-spline surface, rather than to points approximated using the conventional constant curvature method, so the measurements have substantially improved accuracy. The elevation and slope measurements are then blended using weighted least squares fitting techniques. A new b-spline surface is fitted to the blended measurements, with the new surface having substantially improved accuracy in depicting the actual topography of the eye as a result of the elevation-improved accuracy of the slope measurements.

12 Claims, 9 Drawing Sheets

U.S. PATENT DOCUMENTS

| | | | |
|---|---|---|---|
| 4,995,716 | 2/1991 | Warnicki et al. | 351/205 |
| 4,998,819 | 3/1991 | Labinger et al. | 351/212 |
| 5,009,498 | 4/1991 | Gersten et al. | 351/212 |
| 5,018,850 | 5/1991 | Gerstern et al. | 351/212 |
| 5,106,183 | 4/1992 | Yoder, Jr. | 351/211 |
| 5,159,361 | 10/1992 | Cambier et al. | 351/211 |
| 5,194,882 | 3/1993 | Penney | 351/212 |
| 5,214,456 | 5/1993 | Gersten | 351/212 |
| 5,227,818 | 7/1993 | El Hage | 351/221 |
| 5,300,965 | 4/1994 | Kitajima | 351/212 |
| 5,347,331 | 9/1994 | Isogai et al. | 351/212 |
| 5,349,398 | 9/1994 | Koester | 351/212 |
| 5,357,294 | 10/1994 | Shimizu et al. | 351/212 |
| 5,384,608 | 1/1995 | Gersten | 351/212 |
| 5,406,342 | 4/1995 | Jongsma | 351/212 |
| 5,412,441 | 5/1995 | Tibbling et al. | 351/221 |
| 5,414,478 | 5/1995 | van Gelderen | 351/212 |
| 5,416,539 | 5/1995 | Gersten et al. | 351/212 |
| 5,418,582 | 5/1995 | van Saarloos | 351/212 |
| 5,418,714 | 5/1995 | Sarver | 351/212 |
| 5,475,452 | 12/1995 | Kuhn et al. | 351/212 |
| 5,512,965 | 4/1996 | Snook | 351/212 |
| 5,512,966 | 4/1996 | Snook | 351/212 |
| 5,526,072 | 6/1996 | El Hage | 351/212 |
| 5,585,873 | 12/1996 | Shalon et al. | 351/212 |
| 5,865,742 | 2/1999 | Massie | 351/212 |

DEVICE AND METHOD FOR MAPPING THE TOPOGRAPHY OF AN EYE USING ELEVATION MEASUREMENTS IN COMBINATION WITH SLOPE MEASUREMENTS

RELATED APPLICATIONS

This application is a continuation of application Ser. No. 08/841,534, filed Apr. 24, 1997, pending, the contents of which are incorporated by this reference.

TECHNICAL FIELD

This invention relates generally to devices and methods for mapping the topography of an eye, such as the human eye, for purposes such as fitting a contact lens to the eye, pre- and post-operative evaluation of the eye, and diagnosis of abnormalities of the eye, such as astigmatism, keratoconus, and corneal warpage induced by contact lenses. More specifically, this invention relates to devices and methods that utilize elevation measurements of the eye to improve slope measurements of the eye, and that utilize the improved slope measurements in combination with the elevation measurements to provide enhanced mapping of the topography of the eye.

BACKGROUND

One conventional device for mapping the topography of an eye is referred to as a "Placido." As shown in respective front and side views in FIGS. 1A and 1B, a Placido 10 typically includes a series of illuminated concentric rings 12. In order to map the topography of the eye 14, the Placido 10 is positioned in alignment with the eye 14 so the rings 12 reflect off the tear film on the cornea 16 and travel through an aperture 18 in the Placido 10 to a camera 20 that records images of the reflected rings 12 (to clarify the illustration, FIG. 1B depicts the reflection of only some of the rings 12 off the cornea 16). Analysis of these recorded images, including analysis of the shape and position of the reflected rings 12, provides an approximation of the slope of the eye 14 at the points on the eye 14 where the rings 12 were reflected. A surface suitable for display can then be mathematically "fit" to the approximate slopes at these points using various techniques well-known to those of skill in the art.

As shown in more detail in a top view in FIG. 2, analysis of the recorded image of a point P on one of the rings on the Placido 10 reflecting off the cornea 16 of the eye 14, passing through the aperture 18 in the Placido 10, and striking a Charge Coupled Device (CCD) 30 in the camera 20 at point I proceeds as hereinafter described. A central portion 32 of the cornea 16, enclosed by the innermost ring of the Placido 10 reflecting off the cornea 16, is approximated by fitting the central portion 32 with a partial sphere having a radius of curvature $R_0$. Also, the apex point $E_0$ of the cornea 16 is assumed to have a Normal 36 (i.e., an orthogonal vector) that is coincident with the optical axis 38 of the camera 20. The point $E_1$ on the cornea 16 where point P reflects off the cornea 16 is then approximated by assuming a constant curvature between ring edges on the cornea 16.

Using this "constant curvature" technique, a radius of curvature $R_1$ and coordinates $(x_1, z_1)$ are determined iteratively for point $E_1$ such that a Normal 40 at point $E_1$ has equivalent angles of incidence $\alpha$ and reflection $\theta$. The surface of the cornea 16 between points $E_0$ and $E_1$ is then assumed to be a partial sphere having radius of curvature $R_1$. This process is repeated until (x,z) coordinates and a Normal are approximated for all points of reflection of the rings of the Placido 10 off the cornea 16. Knowledge of the Normal of each of these points then permits the calculation of a slope at each point and, in turn, the fitting of a surface to the points as previously described. More information regarding the general operation of Placidos may be found in U.S. Pat. No. 3,797,921 to Kilmer et al.

Because the described Placido utilizes certain assumptions about the eye being measured that are not necessarily true, namely, that the curvature of the cornea between successive Placido rings is constant, and that the surface normal at the apex of the cornea is coincident with the focal axis of the camera, the Placido is not as accurate as is desirable. Consequently, other techniques have been devised for more accurately mapping the topography of an eye.

One such technique, referred to as "ORBSCANI," was introduced by the Assignee of the present invention, Orbtek, Inc. of Salt Lake City, Utah, and is disclosed and claimed in U.S. Pat. Nos. 5,512,965 and 5,512,966 to Snook. As shown in a top view in FIG. 3 herein, in this technique, a first slit beam 50 of light is stepped from right to left across an eye 52 that is to be mapped, and a second slit beam of light (not shown) then steps from left to right across the eye 52. When the first slit beam 50 reaches the anterior surface 54 of the cornea 56 of the eye 52, it splits into two components: a specular reflection 58 from the anterior surface 54 of the cornea 56, and a refracted beam 60 that penetrates the cornea 56 and is refracted (i.e., bent), in accordance with Snell's Law, by the index of refraction between air and the cornea 56. The specular reflection 58 serves no purpose in this technique.

The refracted beam 60 is scattered within the cornea 56 by a mechanism known as diffuse scattering. Reflections 62 from the intersection point $C_{ant}$ between the diffusely scattered refracted beam 60 and the anterior surface 54 of the cornea 56, and reflections 64 from the intersection point $C_{post}$ between the diffusely scattered refracted beam 60 and the posterior surface 66 of the cornea 56, then travel through the focal point of a lens 68 to impinge on a CCD 70 of a camera 72 at respective points $L_{ant}$ and $L_{post}$. Because the relative positions of the light source (not shown) for the first slit beam 50, the eye 52, the lens 68, and the CCD 70 are known, the reflections 62 impinging on the CCD 70 at known point $L_{ant}$ allow calculation of the space coordinates $(x_{ant}, y_{ant}, z_{ant})$ of the point $C_{ant}$. Also, the reflections 64 impinging on the CCD 70 at known point $L_{post}$, as well as knowledge of the index of refraction between air and the cornea 56, allow calculation of the space coordinates $(x_{post}, y_{post}, z_{post})$ of the point $C_{post}$. A similar diffuse reflection 74 from the lens 76 of the eye 52, and from the iris 78 of the eye 52 (diffuse reflection not shown from the iris 78), along with knowledge of the index of refraction between the cornea 56 and the anterior chamber 83 of the eye 52, allow calculation of the space coordinates (x, y, z) of points along the respective anterior surfaces 80 and 82 of the lens 76 and the iris 78. Of course, the second slit beam works in the same manner to measure space coordinates (x, y, z) as the first slit beam 50.

By stepping a pair of slit beams across the eye 52 from left to right and from right to left, this technique allows the direct measurement of space coordinates (x, y, z) for thousands of points on the anterior 54 and posterior 66 surfaces of the cornea 56, and on the anterior surfaces 80 and 82 of the lens 76 and the iris 78. Surfaces suitable for viewing can then be mathematically fit to these known points as previously described. Since no assumptions are made regarding the shape of the cornea 56, lens 76, or iris 78, the technique more accurately portrays the surfaces of these parts of the eye 52.

Unfortunately, inaccuracies exist in this technique as well. In particular, limitations in the density of pixels on the CCD 70, and errors in the relative positions of the first slit beam 50, the eye 52, the lens 68, and the camera 72, limit the accuracy of the measurements using this technique typically to about ±2 μm (micrometers or "microns").

Therefore, there is a need in the art for an improved device and method for mapping the topology of an eye.

DISCLOSURE OF THE INVENTION

In a preferred method of the present invention for mapping the topography of an eye, elevation measurements of the eye are collected using a slit beam diffuse reflection system, such as the ORBSCAN™ device previously described. An approximating b-spline surface is then fitted to the elevation measurements. Slope measurements of the eye are collected using a Placido as previously described, but the slope measurements are referenced to points on the b-spline surface, rather than to points approximated using the previously described constant curvature method, so the measurements have substantially improved accuracy. The elevation and slope measurements are then blended using least squares fitting techniques. A new b-spline surface is fitted to the blended measurements, with the new surface having substantially improved accuracy in depicting the actual topography of the eye as a result of the improved accuracy of the slope measurements.

More generally, a method and device of the present invention for mapping the topography of at least part of an eye, such as a cornea, include collecting elevation measurements from the eye part. This may be accomplished using elevation measurement systems such as a slit beam diff-use reflection system, a rasterstereography system, or an interferometry system. Slope measurements are then collected from the eye part, either directly, using slope measurement systems such as a Placido or a grid-based reflection system, or indirectly using the previously described elevation measurement systems. The slope measurements may be referenced to the elevation measurements for improved accuracy. The elevation and slope measurements are blended, for example, using weighted least squares fitting techniques, and topography data, such as an approximating b-spline surface, is then determined from the blended measurements.

In another embodiment of the present invention, a computer readable storage medium, such as a computer diskette, includes a stored program for controlling a computer system to operate in accordance with the described method for mapping the topography of an eye.

In a further embodiment, a method for collecting elevation and slope measurements from an eye includes either measuring the elevation measurements and then referencing measurement of the slope measurements from the measured elevation measurements, or measuring the slope measurements and then referencing measurement of the elevation measurements from the measured slope measurements.

In still another embodiment, another method for mapping the topography of an eye includes collecting elevation or slope measurements from the eye. An ultrasound device is then calibrated to the eye using the collected measurements. For example, a measurement of the anterior chamber depth of the eye by the ultrasound device may be calibrated to a measurement of the anterior chamber depth derived from the collected measurements. Measurements of the topography of the eye are then collected using the calibrated ultrasound device.

BEST MODE FOR CARRYING OUT THE INVENTION

The inventors have recognized that elevation measurements of an eye (e.g., those collected using the slit beam technique previously described) may be used to enhance the accuracy of slope measurements of the eye (e.g., Placido measurements as previously described) by eliminating the need to make assumptions of the type previously described in the collection of the slope measurements. The improved slope measurements may then be used in combination with the elevation measurements to more accurately approximate the surface of the eye.

Figure 1A:
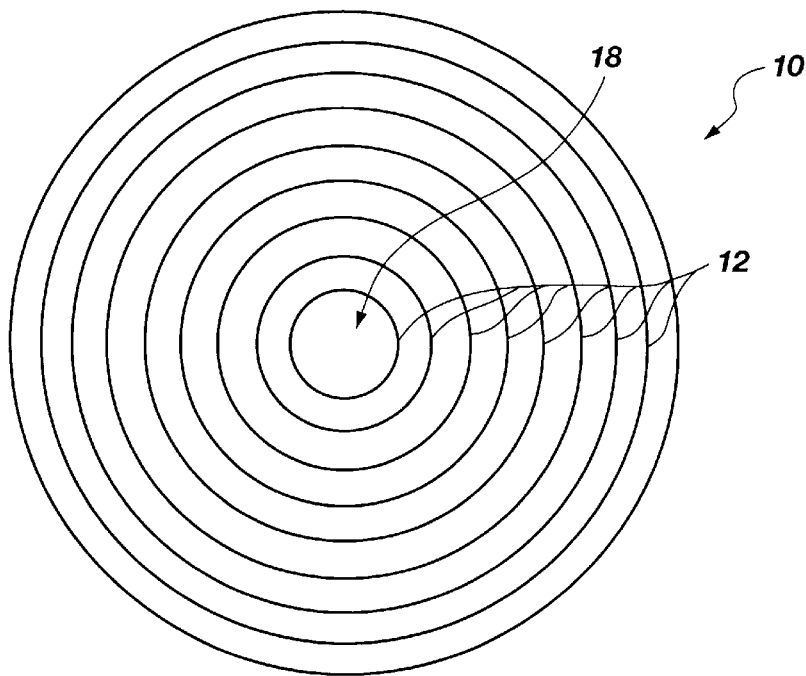
FIGS. 1A and 1B are respective front and side views of a conventional device, referred to as a "Placido," measuring the slope of the cornea of an eye.
Figure 1B:
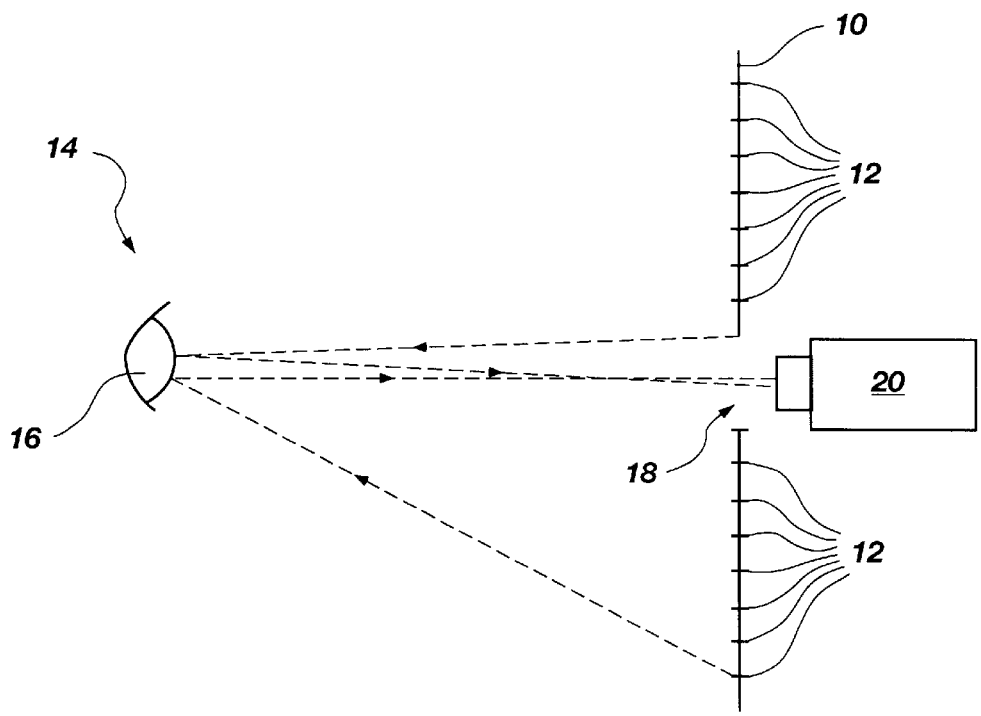
Figure 2:
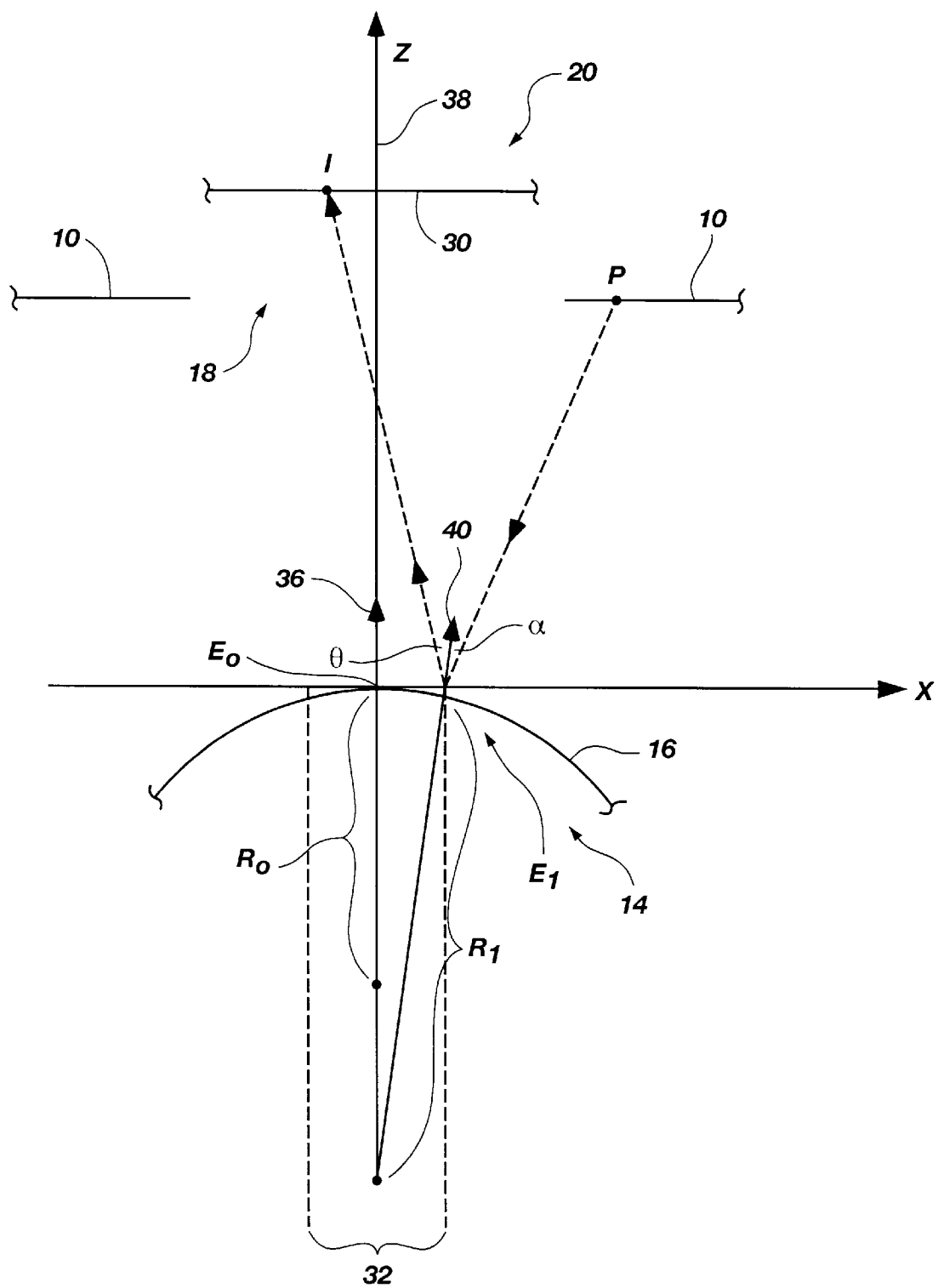
FIG. 2 is a top and diagrammatic view of the Placido of FIGS. 1A and 1B.
Figure 3:
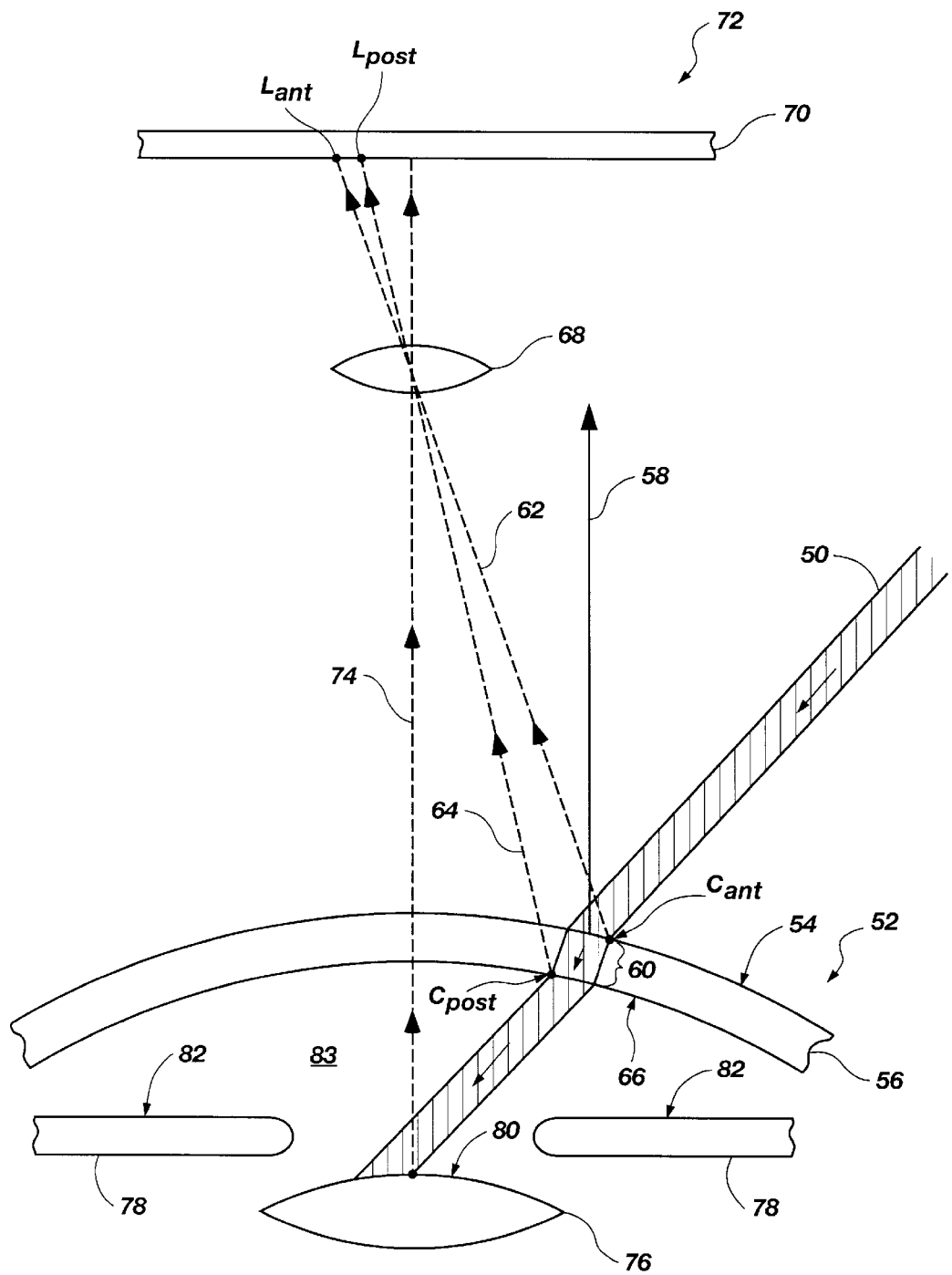
FIG. 3 is a top view of a conventional slit beam system for directly measuring the elevation of various points on the cornea, iris, and lens of an eye.
Figure 4A:
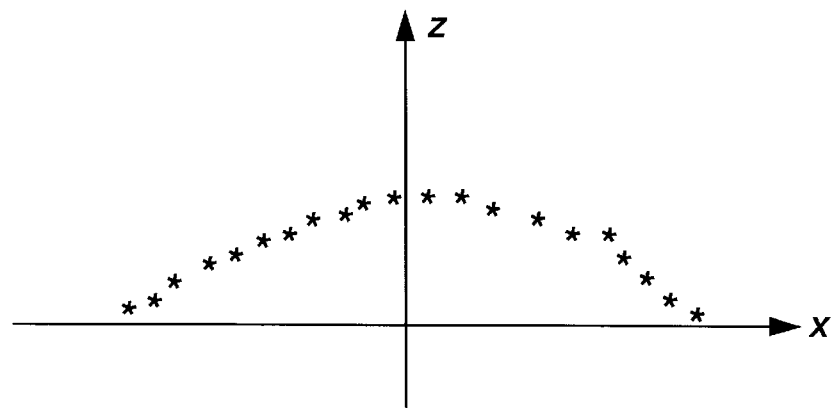
FIGS. 4A, 4B, and 4C are top views of elevation and slope measurements of an eye made in accordance with the present invention.

For example, a selected xz-plane "slice" of elevation measurement points (represented by "*") on the anterior surface of the cornea of an eye measured using the slit beam technique previously described is shown in a top view in FIG. 4A. Each of these points (*) has measured space coordinates (x, y, z) as previously described. As shown in a top view in FIG. 4B, an approximating b-spline surface 84 has been fitted to the elevation measurement points (*) of FIG. 4A using conventional techniques in order to approximate the anterior surface of the cornea of the eye. As shown in a top view in FIG. 4C, a point P on the ring of a Placido (not shown in FIG. 4C) reflects off a point E on the b-spline surface 84 and impinges on a CCD 86 at point 1. Because the relative positions of the CCD 86, the Placido point P, and the b-spline surface 84 are known, and because the space coordinates (x, y, z) of point E are known, knowledge of point I on the CCD 86 allows direct calculation of the normal 88 of the b-spline surface 84 at point E. Repeating this process for every Placido point on every ring of the Placido provides a comprehensive set of Normals for many points on the b-spline surface 84, and hence provides a comprehensive set of slope measurements for many points on the b-spline surface 84. Because these slope measurements are made without resort to the approximations previously described with respect to the constant curvature technique, the measurements are more accurate than conventional slope measurements collected using a Placido.

Figure 4B:
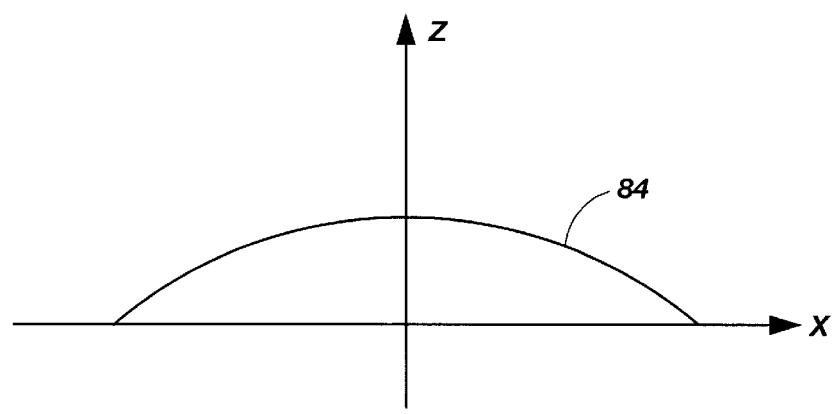
Figure 4C:
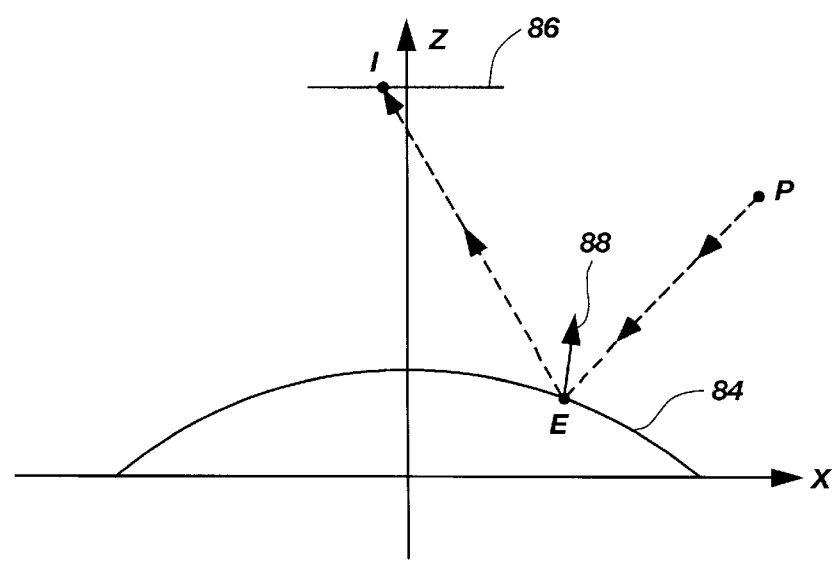
Figure 5A:
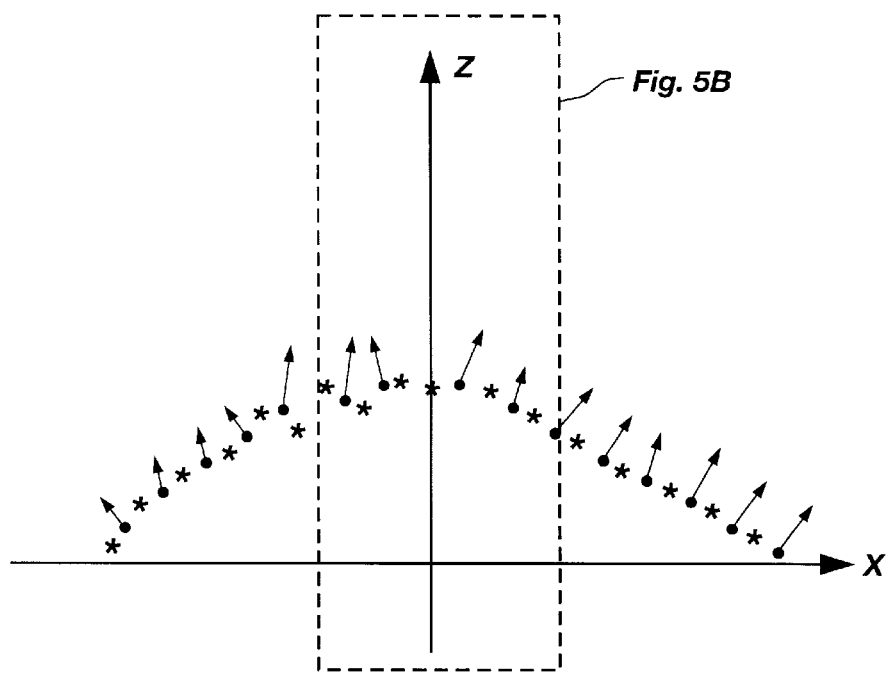
FIG. 5A is a top view of the elevation and slope measurements of FIGS. 4A, 4B, and 4C.
Figure 5C:
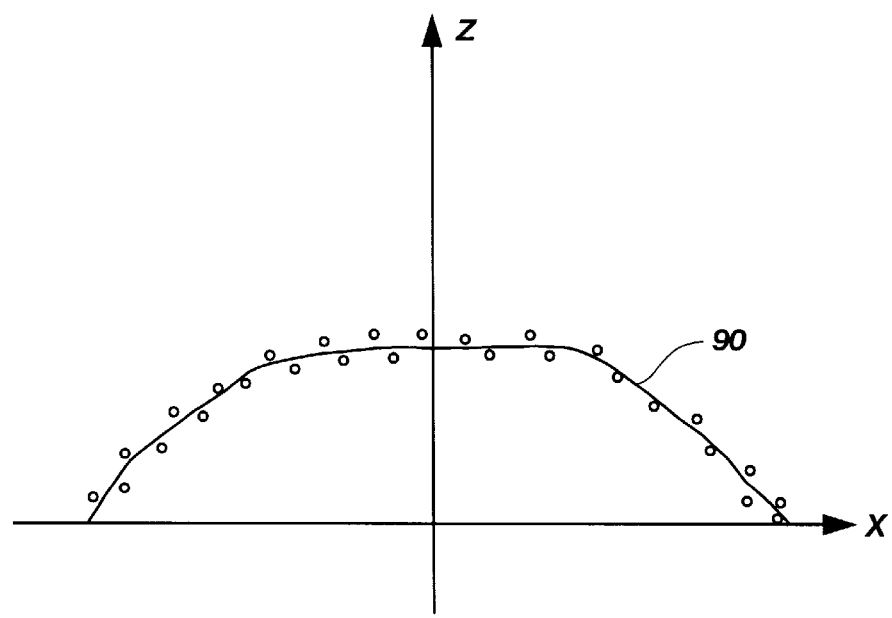
FIG. 5C is a top view of an improved, more accurate b-spline surface approximating the control points of FIG. 5B in accordance with the present invention.
Figure 5B:
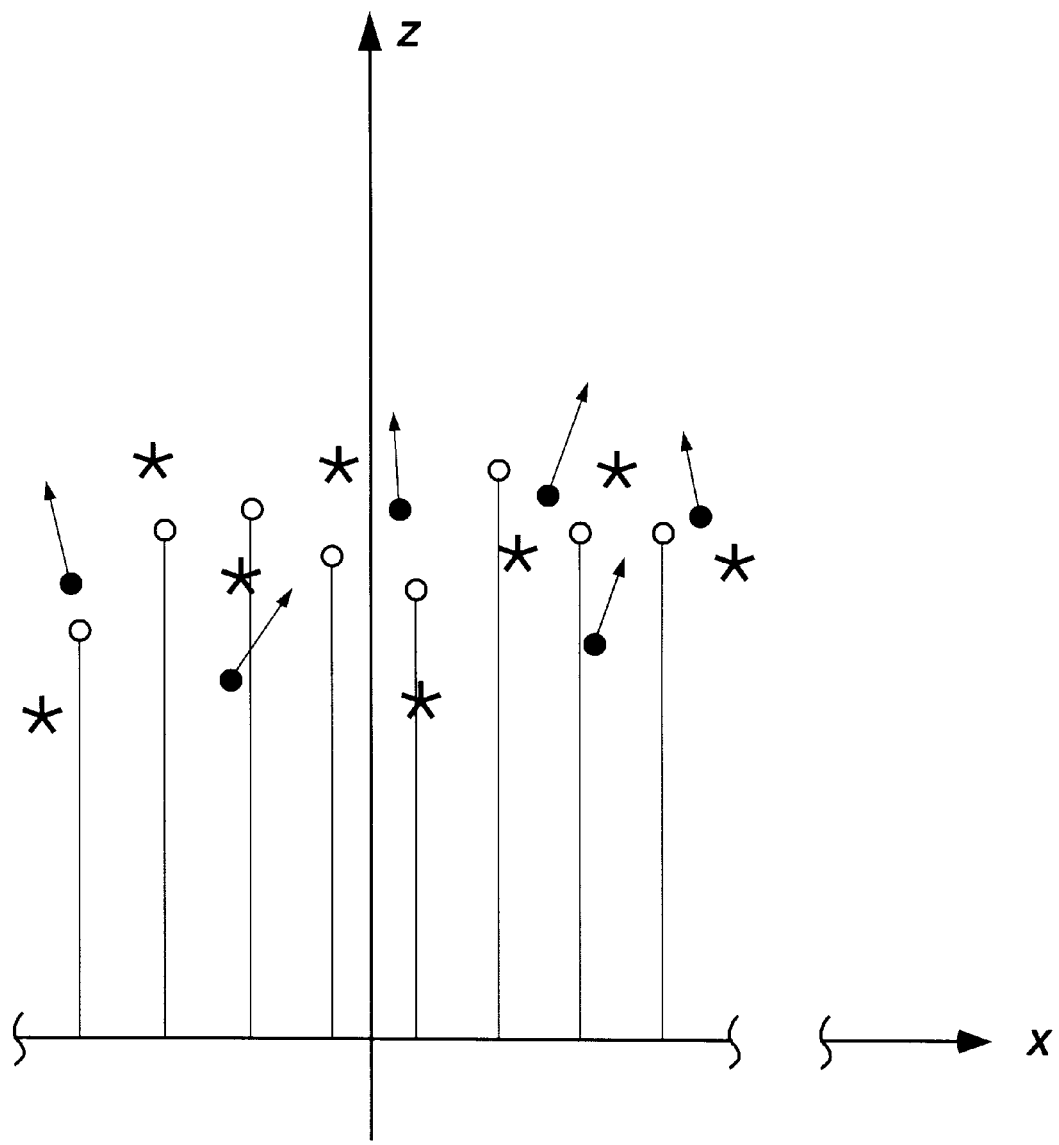
FIG. 5B is a more detailed top view of the measurements of FIG. 5A and of b-spline control points generated in accordance with the present invention by weighted least squares fitting the elevation and slope measurements.

As shown in a top view in FIG. 5A, the elevation measurement points (*) and the slope measurement points (represented by "♂," with the arrow portion of the symbol representing the Normal at a particular point) previously described with respect to FIGS. 4A, 4B, and 4C generally define the outline of the anterior surface of the measured eye. These points are shown in a more detailed top view in FIG. 5B. In addition, control points (represented by "o" and not shown in FIG. 5A for purposes of clarity) are shown in FIG. 5B for a new approximating b-spline surface (see FIG. 5C). These control points (o) are calculated in accordance with the invention by performing a weighted least squares fit of the elevation (*) and slope (♂) measurement points, with the more accurate of the two sets of measurement points being weighted more heavily so the position of the control points (o) is more heavily influenced by the more accurate measurement points. As shown in a top view in FIG. 5C, a new approximating b-spline surface 90 is calculated in accordance with the invention to fit the control points (o). Because the b-spline surface 90 uses the slope measurement points (see FIGS. 5A and 5B) in combination with the elevation measurement points (see FIGS. 5A and 5B), it is a substantially more accurate depiction of the actual anterior surface of the eye than the b-spline surface 84 of FIGS. 4B and 4C.

Figure 6:
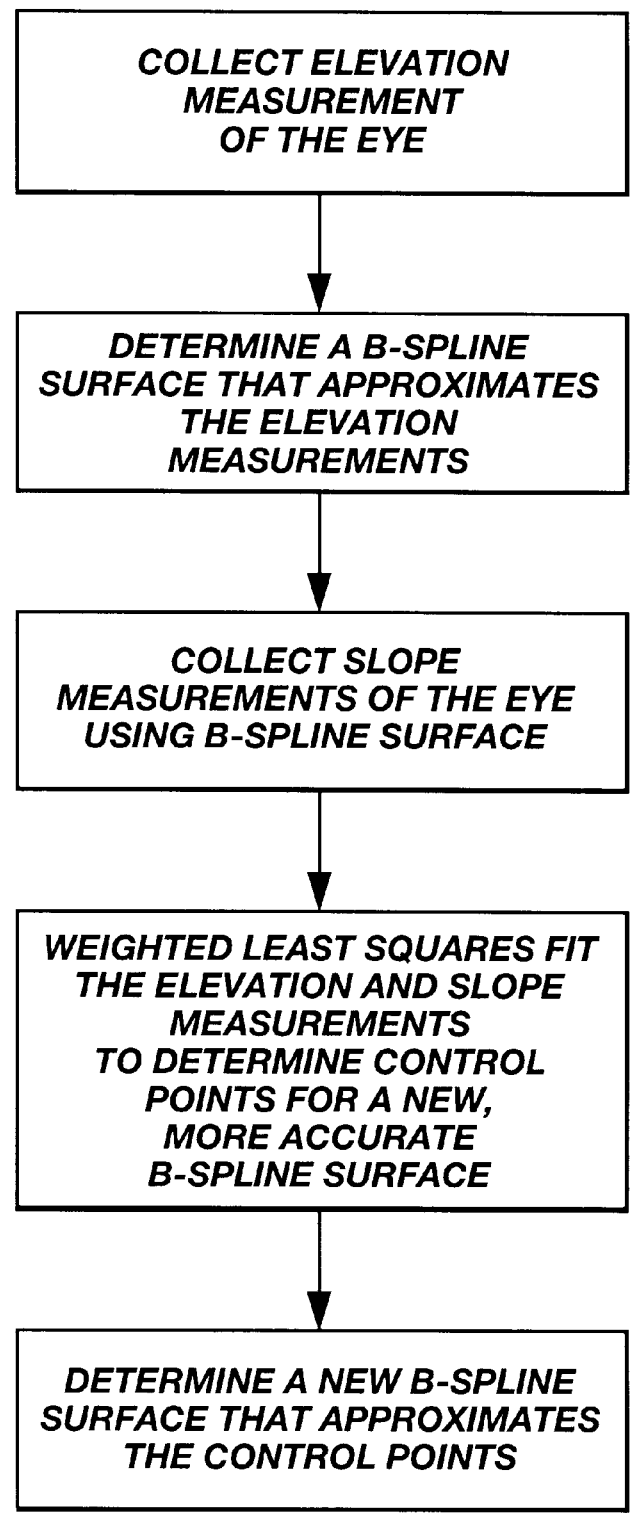
FIG. 6 is a flow chart of a method of the present invention.

As shown in a flow chart in FIG. 6, one method of the present invention begins with collecting elevation measurements of the anterior surface of the cornea of an eye that is to be mapped. Such measurements are preferably collected using a pair of slit beams as previously described. However, any method for measuring elevation data will work for purposes of the present invention, including slit beam systems with a single slit beam or with more than two slit beams, and other elevation measurement systems, such as rasterstereography systems in which different views of a grid point projected onto the cornea are triangulated to measure the (x, y, z) coordinates of the point, and interferometry systems.

The elevation measurements are then used to approximate the anterior surface of the cornea. Preferably, a well-known approximating b-spline surface is used, although any method for approximating a surface using the elevation measurements will work for purposes of the present invention, including well-known modeling techniques such as the 2D rational polynomial method, the Zernike polynomial method, the 2D polar method, the 2D spline method, the Bezier-spline method, and the algebraic surfaces method.

Whichever method is used to approximate the anterior surface of the cornea, the approximated surface is then used as the basis for collecting measured slope data for the anterior surface of the cornea. Preferably, a Placido device is used to measure the slope information, resulting in slope measurements of substantially enhanced accuracy. However, any method for measuring slope information will work for purposes of the present invention, including projected grid-based systems, and devices for directly measuring elevation information and thereby indirectly measuring slope information.

With the elevation and slope Measurements in hand, the measurements are least squares fitted in order to arrive at a series of control points that represent a "blending" of the elevation and slope measurements. The least squares system (i.e., a matrix system [A][x]=[b]) typically will require deflation to eliminate unconstrained control points so the system is full rank and square. After deflation, Cholesky decomposition is preferably used to solve for the control points, although Gaussian elimination will also work. See Press et al., "Numerical Recipes in C: The Art of Scientific Computing," Cambridge University Press, 1988, for more information regarding the Cholesky decomposition. If the Cholesky decomposition is unsuccessful, then the more calculation-intensive Singular Value Decomposition (SVD) will be necessary to solve the system for the control points. See Kahaner et al., "Numerical Methods and Software," Prentice Hall, 1989, for more information regarding the SVD.

Notwithstanding the foregoing, any method for least squares fitting the elevation and slope measurements to arrive at the control points will work for purposes of the present invention. Also, it should be understood that other methods for blending or "smoothing" the elevation and slope measurements fall within the scope of the present invention.

With the control points calculated, a new surface is fitted to the control points to more accurately approximate the anterior surface of the cornea. Preferably, the new surface is an approximated b-spline surface, although the wide variety of other surfaces previously specified will also work at this stage of the inventive method.

Figure 7:
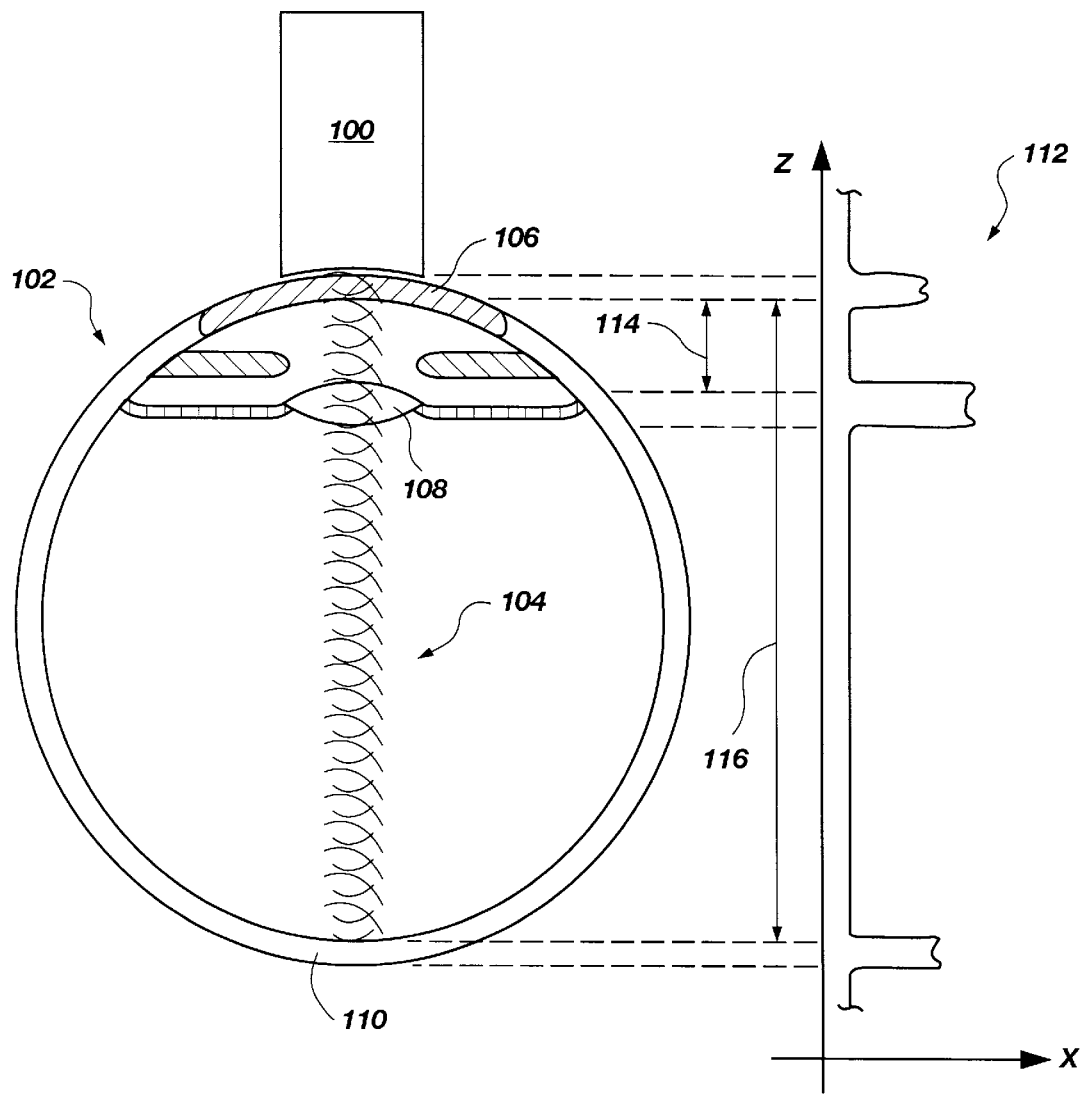
FIG. 7 is a top sectional view of an improved ultrasound retinal mapping device in accordance with the present invention.

As shown in a top sectional view in FIG. 7, operation of an ultrasound device 100 for mapping interior surfaces of an eye 102 may be improved using the methods of the present invention. Conventionally, an ultrasound beam 104 from the ultrasound device 100 can roughly detect the thickness of the cornea 106, the lens 108, and the retina 110, and distances between the cornea 106, the lens 108, and the retina 110, as shown in a graph 112 of reflections from the beam 104 as it passes through the eye 102. However, because the wavelength of the ultrasound beam 104 is relatively long, these measurements are indeed rough. By using the present invention's much more precise measurement of the anterior chamber depth 114 (i.e., the distance from the posterior surface of the cornea 106 to the anterior surface of the lens 108) to calibrate measurement of the anterior chamber depth 114 by the ultrasound device 100, other measurements of the ultrasound device 100 within the eye 102, such as the focal length 116 of the eye 102 (i.e., the distance from the cornea 106 to the retina 110), are substantially improved.

Figure 8:
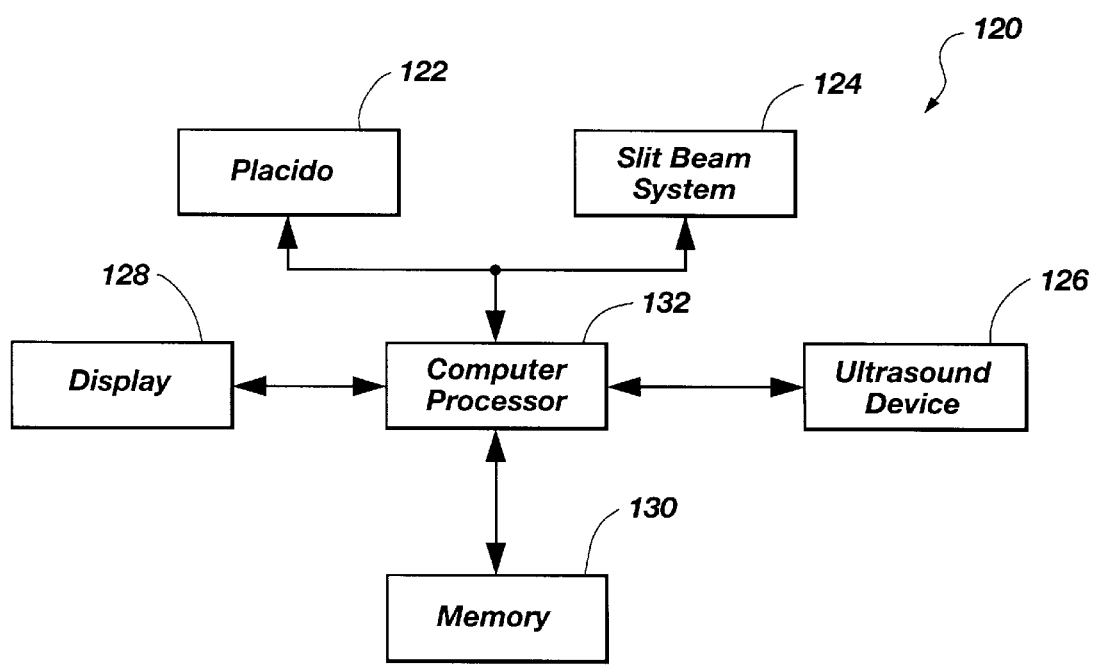
FIG. 8 is an eye mapping system in accordance with the present invention.

As shown in FIG. 8, the present invention is implemented in an eye mapping system 120 including a Placido 122, a slit beam elevation measurement system 124, an ultrasound device 126, a computer display 128, and a computer memory 130, all interconnected with a computer processor 132. Of course, it should be understood that methods of the present invention may be implemented in software stored in the computer memory 130, and that the computer memory 130 may comprise any computer readable storage medium, including diskettes and CD-ROM's. It should also be understood that a second Placido may replace the slit beam system 124.

Although the present invention has been described with reference to a preferred embodiment, the invention is not limited to this embodiment. For example, although certain steps of the inventive method have been specified as occurring in a particular order, it should be understood that these steps need not necessarily occur in this order. Thus, for example, when approximated b-spline surfaces are used, the new, more accurate surface may be calculated in "real" time while successive slope measurements are collected. Also, although the present invention has been described principally as improving the accuracy of approximations of the anterior surface of the cornea, it should be understood that the present invention is also applicable to improve mapping of the topography of the iris and lens of the eye. Thus, the invention is limited only by the appended claims, which include within their scope all equivalent devices and methods that operate according to the principles of the invention as described.

What is claimed is:

1. A method for collecting elevation and slope measurements from an eye, the method comprising:

measuring one of the elevation and slope measurements; and measuring the other of the elevation and slope measurements by referencing the one of the elevation and slope measurements.

2. The method of claim 1 further comprising fitting an approximating surface to the elevation measurements, wherein the step of measuring the other of the elevation and slope measurements comprises measuring the slope measurements by referencing the approximating surface fitted to the elevation measurements.

3. A method of obtaining slope measurements from an eye comprising:

measuring elevation of the eye to obtain elevation measurements;

fitting a surface to said elevation measurements; and measuring slope of said eye with a slope measuring system and referencing said surface to obtain slope measurements.

4. The method of claim 3, wherein said measuring elevation of the eye is performed using a slit beam diffuse reflection system.

5. The method of claim 4, wherein said slit beam diffuse reflection system is an ORBSCAN™ device.

6. The method of claim 3 wherein said measuring elevation of the eye is performed using a rasterstereography system.

7. The method of claim 3, wherein said measuring elevation of the eye is performed using an interferometry system.

8. The method of claim 3 wherein said surface is an approximating b-spline surface.

9. A method for mapping the topography of an eye, the method comprising:

measuring the elevation of an eye to obtain elevation measurements;

fitting a first surface to said elevation measurements;

measuring slope of said eye with a slope measuring system and referencing said first surface to obtain slope measurements;

blending said elevation measurements with said slope measurements to obtain blended measurements;

calculating anterior chamber depth from said elevation measurements, said slope measurements and said blended measurements;

measuring anterior chamber depth with an ultrasound device; and calibrating said ultrasound device based on the difference between said calculated anterior chamber depth and said measured anterior chamber depth.

10. An apparatus for mapping the topography of at least a part of an eye, the apparatus comprising:

a Placido for obtaining slope measurements of at least a part of an eye;

a slit beam system for obtaining elevation measurements of said at least a part of an eye;

a computer processor coupled to said Placido and said slit beam system for processing said slope measurements and said elevation measurements to obtain blended measurements and the topography of at least a part of an eye;

an ultrasound device coupled to said computer processor for measuring certain characteristics of said at least a part of an eye wherein said computer processor is configured calibrate said ultrasound device based on said elevation measurements, said slope measurements, and said blended measurements.

11. The apparatus of claim 10 further comprising a display coupled to said computer processor for displaying the topography of at least a part of an eye.

12. The apparatus of claim 11, further comprising a memory for storing data.

* * * * *